(12) United States Patent
Lücke et al.

(10) Patent No.: US 10,314,524 B2
(45) Date of Patent: Jun. 11, 2019

(54) DIAGNOSTIC ANALYTE COLLECTION DEVICE BASED ON FLEXIBLE POLYMERS WITH BIOLOGICAL SURFACE MODIFICATION AND MICROFLUIDIC FUNCTIONALITY

(75) Inventors: Klaus Lücke, Potsdam OT Golm (DE); Ekkehardt Weber, Potsdam OT Golm (DE); Robert Müller, Potsdam OT Golm (DE); Andreas Bollmann, Potsdam OT Golm (DE); Oliver Harnack, Potsdam OT Golm (DE)

(73) Assignee: GILUPI GMBH, Potsdam Ot Golm (DE)

( * ) Notice: Subject to any disclaimer, the term of this patent is extended or adjusted under 35 U.S.C. 154(b) by 1571 days.

(21) Appl. No.: 13/120,592

(22) PCT Filed: Sep. 23, 2009

(86) PCT No.: PCT/EP2009/006883
§ 371 (c)(1),
(2), (4) Date: Aug. 4, 2011

(87) PCT Pub. No.: WO2010/034484
PCT Pub. Date: Apr. 1, 2010

(65) Prior Publication Data
US 2011/0301442 A1 Dec. 8, 2011

(30) Foreign Application Priority Data

Sep. 23, 2008 (EP) .................................. 08075779

(51) Int. Cl.
*A61B 5/1495* (2006.01)
*A61B 5/145* (2006.01)
(Continued)

(52) U.S. Cl.
CPC .......... *A61B 5/145* (2013.01); *A61B 5/14546* (2013.01); *A61B 10/02* (2013.01); *G01N 33/54366* (2013.01)

(58) Field of Classification Search
CPC ....................................................... A61B 5/00
(Continued)

(56) References Cited

U.S. PATENT DOCUMENTS 5,916,173 A * 6/1999 Kirsner ......................... 600/551
6,342,041 B1 * 1/2002 Saint-Ramon et al. ...... 600/551
(Continued)

FOREIGN PATENT DOCUMENTS

WO    WO 2006/131400         12/2006

OTHER PUBLICATIONS

International Search Report (PCT/ISA/210) for PCT/EP2009/006883 dated Jan. 25, 2010.
(Continued)

*Primary Examiner* — May A Abouelela
(74) *Attorney, Agent, or Firm* — Buchanan Ingersoll & Rooney PC

(57) ABSTRACT

The invention relates to a device for detecting analytes. In order to supply a need in alternative prenatal diagnostic methods which do not include the risks known in the state of art, the present invention provides a device for detecting analytes, including a polymer fiber and capturing molecules, wherein the capturing molecules bind to an analyte and/or a linker molecule.

34 Claims, 6 Drawing Sheets

Figure 1:
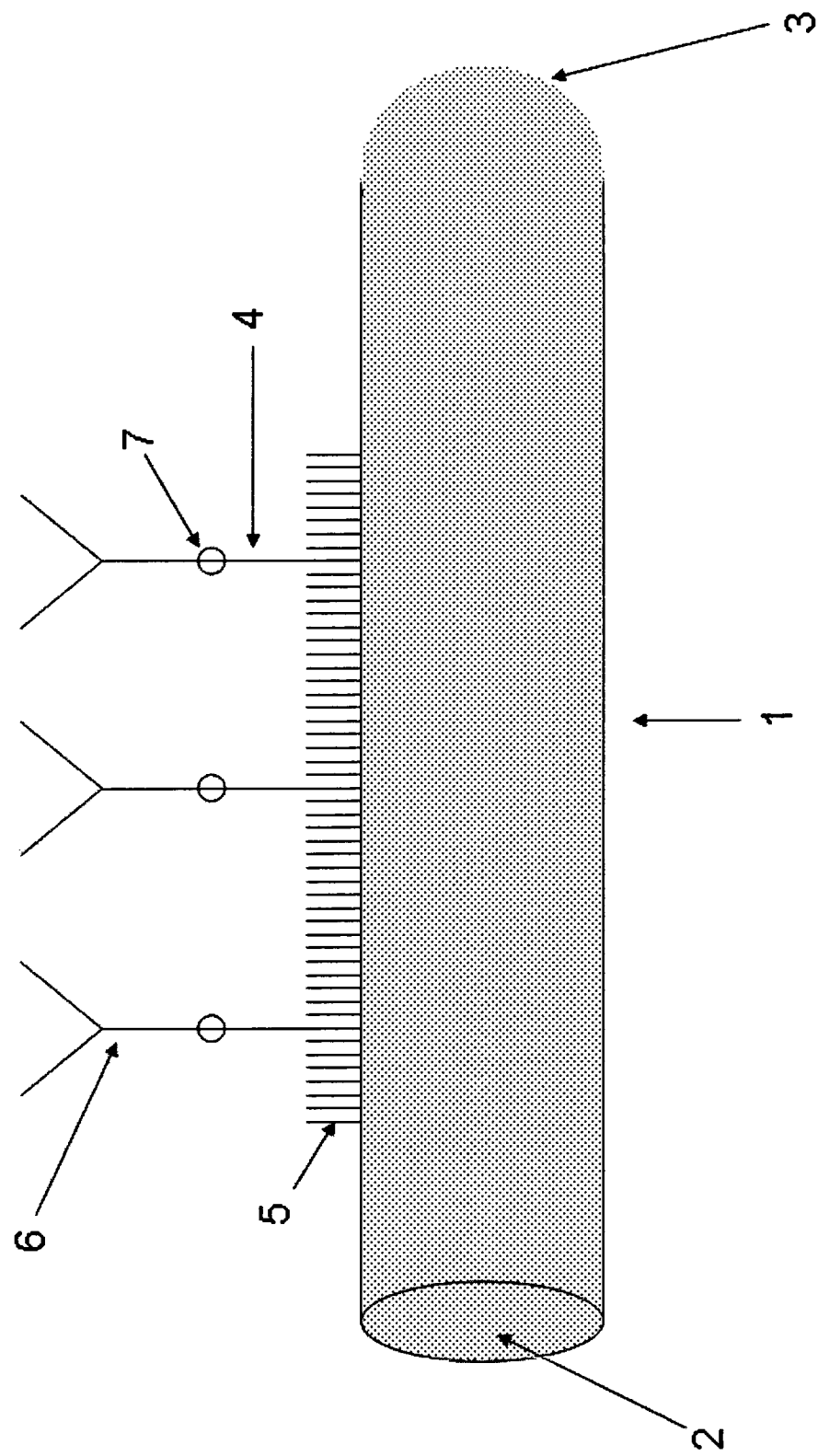

(51) Int. Cl.
*A61B 10/02* (2006.01)
*G01N 33/543* (2006.01)

(58) Field of Classification Search
USPC .................................. 600/551, 309; 506/12
See application file for complete search history.

(56) References Cited

U.S. PATENT DOCUMENTS

| | | | | |
|---|---|---|---|---|
| 6,440,662 | B1* | 8/2002 | Gerwen | C12Q 1/6816 204/412 |
| 2003/0148401 | A1* | 8/2003 | Agrawal | B01J 19/0046 506/9 |
| 2005/0003559 | A1* | 1/2005 | Weber et al. | 436/526 |
| 2007/0227907 | A1* | 10/2007 | Shah | G01N 27/307 205/777.5 |
| 2008/0213130 | A1* | 9/2008 | Pison et al. | 422/68.1 |
| 2009/0054262 | A1* | 2/2009 | Abbott et al. | 506/12 |
| 2009/0131274 | A1* | 5/2009 | Pison et al. | 506/12 |
| 2010/0001210 | A1* | 1/2010 | Klunder | G01N 21/648 250/461.1 |
| 2010/0168609 | A1* | 7/2010 | Pison et al. | 600/562 |

OTHER PUBLICATIONS

H. Wei et al., "Sensitive detection of antibody against antigen F1 of *Yersinia pestis* by an antigen sandwich method using a portable fiber optic biosensor", Sensors and Actuators B, Oct. 22, 2007, pp. 525-530, vol. 127, No. 2.

H. Wei et al., "Direct detection of *Yersinia pestis* from the infected animal specimens by a fiber optic biosensor", Sensors and Actuators B, Mar. 30, 2007, pp. 204-210, vol. 123, No. 1.

J. Jensen et al., "Selective detection of antibodies in microstructured polymer optical fibers", Optics Express 5883, Jul. 25, 2005, pp. 5883-5889, vol. 13, No. 15.

G. Emiliyanov et al., "Localized biosensing with Topas microstructured polymer optical fiber", Optical Society of America, Mar. 1, 2007, pp. 460-462, vol. 32, No. 5.

J. Kai et al., "Automated fluidic system with a chaotic microfluidic reaction chamber for rapid, multi-analyte immunosensing", Transducers '07 & Eurosensors XXI, 14th International Conference on Solid-State Sensors, Actuators and Microsystems IEEE, 2007, pp. 735-738, Piscataway, New Jersey, USA.

O. Wolfbeis, "Fiber-Optic Chemical Sensors and Biosensors", Analytical Chemistry, May 8, 2008, pp. 4269-4286, vol. 80, No. 12.

* cited by examiner

DIAGNOSTIC ANALYTE COLLECTION DEVICE BASED ON FLEXIBLE POLYMERS WITH BIOLOGICAL SURFACE MODIFICATION AND MICROFLUIDIC FUNCTIONALITY

The invention relates to a novel device structure that is based on a flexible polymer fiber that is decorated with molecular binding sites, so-called capturing molecules, for the binding of various different analyte species.

BACKGROUND

The application of optical fiber, catheter or wire-based devices, which are decorated with biologically active molecules, for diagnostic tasks such as the detection and capturing of DNA, proteins, cells, and others from biological samples or even from living organisms is known in the state of art.

Detection of biomolecules by using fibers is often related to optical detection methods that sense in-situ the attachment of DNA, proteins, cells and others to functionalised and optically transparent surfaces. Fluorescence-based detection, optical absorption, as well as surface plasmon resonances are used. A widely used functionalisation approach in these studies is the attachment of antibodies to the fiber surface by for example silane chemistries. In some cases, the fiber surface is engineered in order to introduce a tapered region, which provides higher sensitivity. The microscale structure of most of the devices consists of a flat surface. Biosensing based on fibers can be used in-vitro and in-vivo and reaches single cell resolution levels.

The catheter-based collection of biological tissue samples from living organisms for the subsequent, ex-situ analysis is a well-known method on the field of biopsy. Catheters are modified with polymeric surfaces or molecular monolayers in order to reduce complications such as venous thrombosis and infections.

WO 2006/131400 teaches the decoration of a stainless steel wire with metallic islands that are modified with antibodies for specific cell capture. The metallic islands with sizes in the 100 nm regime were fabricated by using a sphere-monolayer as a shadow mask during the deposition step of a gold layer. The gold islands were modified with thiolated linker molecules that bind specific antibodies.

Errors that generate too many or too few chromosomes can also lead to disease phenotypes. For example, a missing copy of chromosome X results in Turner's Syndrome, while an additional copy of chromosome 18 or 13 results in Edward's Syndrome or Patau Syndrome, respectively.

One of the most common chromosome abnormalities is known as Down syndrome. The estimated incidence of Down syndrome is between 1 in 1,000 to 1 in 1,100 live births. The vast majority of children with Down syndrome have an extra chromosome 21. Chromosomal abnormalities are congenital, and therefore, prenatal diagnosis can be used to determine the health and condition of an unborn fetus. Specifically, prenatal diagnosis is helpful for managing the remaining term of the pregnancy, planning for possible complications with the birth process, preparing for problems that can occur in the newborn infant, and finding conditions that may affect future pregnancies.

There are a variety of non-invasive and invasive techniques available for prenatal diagnosis including ultrasonography, amniocentesis, chorionic villus sampling (CVS), and the characterization of fetal blood cells from maternal blood, and the determination of maternal serum alpha-fetoprotein, maternal serum beta-HCG, and maternal serum estriol. However, the techniques that are non-invasive are less specific, and the techniques with high specificity and high sensitivity are highly invasive. A common invasive method is amniocentesis (also referred to as amniotic fluid test or AFT), a medical procedure used in prenatal diagnosis of chromosomal abnormalities and fetal infections. A small amount of amniotic fluid, which contains fetal tissues, is extracted from the amnion or amniotic sac surrounding a developing fetus, and the fetal DNA is examined for genetic abnormalities. This procedure is often used to diagnose the Down syndrome. Although the procedure is routine, complications include preterm labor and delivery, respiratory distress, postural deformities, fetal trauma and alloimmunisation, infection of the amniotic sac from the needle, and failure of the puncture to heal properly, which can result in leakage or infection. Serious complications can result in miscarriage. The risk of amniocentesis-related miscarriage is generally thought to be 1 in 200.

Therefore, there is a need in alternative prenatal diagnostic methods which do not include the risks known in the state of art.

The object of the invention was to provide a fiber-based device that not only detects rare bioanalytes inside living organisms or in in-vitro samples, but which detects and catches such analytes in a highly efficient way and preserves or protects them until they can be ex-situ analysed in detail. Also the production costs are supposed to be lower than in the state of art.

SUMMARY OF THE INVENTION

The solution to the above technical problem is achieved by providing the embodiments characterized in the claims.

In a first embodiment the invention relates to a device for detecting analyte species, comprising a polymer fiber and capturing molecules, wherein the capturing molecules bind to an analyte and/or a linker molecule.

Fibers based on polymeric materials are preferred because of their advantageous mechanical properties and their wide range of various biofunctionality. Most device structures in the state of art require a metallisation step or even a patterning step to form discrete anchor points of the capturing molecules. These features cause costs and in addition, for in-vivo applications, the presence of metals represents a certain risk factor. The device of the invention can be produced without high fabrication costs, which for example allows the use of these devices in daily routine tests.

In the state of art metallisation with gold is common procedure. Surprisingly by avoiding the presence of gold the risk of harmful contamination of the patient's body was reduced considerably.

The fiber of the invention is decorated with biologically active capturing molecules that are designed to either bind first to (biocompatible) linker molecules and subsequently capture the specific analyte molecules, or directly capture the specific analyte molecules. Linkers can help to present the biologically active capturing molecules in a specifically orientated manner. Linkers can also prevent the surface-induced degradation of the biologically active capturing molecule and may reduce the unspecific binding of molecules which are not the target of the capturing molecules.

The device of the invention can be applied for the collection of various different analytes for both in-vitro and in-vivo applications. The functionalised polymeric fiber with microstructures or surface geometries on the surface can be introduced into the biological sample, such as a blood sample or into a vein of a living organism. During a period of at least a few seconds and several hours, the fiber collects through its biofunctional coating the respective target analyte. After the collection process has finished, the fiber is retracted and the captured material is separated from the fiber for analysis.

Also preferred is the device wherein the polymer fiber is flexible. A major problem in the prior art are that fibers for example in form of a stainless steel wire are not flexible enough if it comes to in-vivo analyte collection applications. Especially dangerous is the use of inflexible fibers for applications into a vein. The risk of rupture of the vein or other biological tissue by the fiber is high. The fibers of the invention are highly flexible or soft and therefore help to avoid injuries. A flexible structure can easily follow the biological boundaries of for example the inner walls of veins.

In another preferred embodiment the invention relates to a device, wherein the polymer fiber has the basic shape of a cylinder or a tube. These shapes are especially advantageous, because they do not include any edges. Surprisingly a cylindrical fiber leads to less injuries in in-vivo diagnosis. Also the capturing molecules can be arranged in a better way if a fiber with a shape of a cylinder or a tube is used. Therefore, analytes can be captured more efficiently.

Also preferred is the device, wherein the fiber is round-shaped or bow-shaped at one or both ends of the fiber. In terms of the invention the ends of a cylinder or a tube are the surface and the base. By introducing one or two bow-shaped ends the whole fiber becomes streamlined. This is especially advantageous for the in-vivo use of the device. Also preferred is the device wherein one end is round-shaped and the other end is bow-shaped. The bow-shaped end is superior for the introduction into an organism for example into a vein.

Especially preferred is a device, wherein the diameter of the fiber is 100 μm to 3 mm, preferred 500 μm to 1 mm. Fibers with these sizes can be used for in-vivo and in-vitro applications, which is advantageous because no extra production is needed. Fibers with a bigger diameter are especially advantageous for in-vitro applications because a lot of capturing molecules can be introduced, which improves the detection of analytes. Fibers with a very small diameter are superior for in-vivo detections, when the vessel is small as well. Injuries can be avoided and the patient does not feel any discomfort.

In an also preferred embodiment the fiber comprises a material selected from the group comprising nylon, polyimide, Teflon, polyurethane, polystyrene, polyethylene, epoxy, polycarbonate and/or composite materials hereof. These materials provide a very low risk of micro injuries during in-vivo application. Another advantage of these materials is the low production cost compared to metalized devices known in the state of art.

Also preferred is the device, wherein the capturing molecules are selected from the group comprising antibodies, antigens, receptors, polynucleotides, DNA probes, RNA probes, polypeptides, proteins and/or cells. Any capturing molecule that can bind an analyte target or a linker molecule can be used in the invention. The affinity interaction between the capturing molecule and the analyte is based on specific receptor-ligand or antibody-antigen interaction, unspecific adhesion, or on physical attraction between the device and the analyte species of interest. The capturing molecules are designed in a way that (biocompatible) linkers can be bound via amine bonds, chelate complexation, ionic/electrostatic bonds or any other covalent bonds. The layer of capturing molecules is also referred to as "guest layer".

In terms of the invention "antibody" refers to an intact antibody, or a fragment thereof, that could compete with the intact antibody for specific binding. An antibody or fragment thereof is said to specifically bind an antigen when the dissociation constant is less than or equal to 1 μM, preferably less than or equal to 100 nM and most preferably less than or equal to 10 nM. Binding can be measured by methods known to those skilled in the art. Antibody fragments comprise a portion of an intact antibody, preferably the antigen binding or variable region of the intact antibody. Binding fragments include Fab, Fab', F(ab')2, and Fv fragments; diabodies; linear antibodies; single-chain antibody molecules; and multispecific antibodies formed from antibody fragments, recombinant and synthetic antibodies, antibody-like binding proteins or receptors or receptor-like molecules. An antibody other than a "bispecific" or "bifunctional" antibody is understood to have each of its binding sites identical.

"Polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

In terms of the invention "polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids at commonly referred to as the 20 naturally occurring proteinogenic amino acids, and that many amino acids, including the terminal amino acids, may be modified in a given polypeptide, either by natural processes such as glycosylation and other post-translational modifications, or by chemical modification techniques which are well known in the art. Common modifications include glycosylation, lipid attachment, sulfation, gamma-carboxylation of glutamic acid residues, hydroxylation and ADP-ribosylation, and these and others are described in most basic texts.

A common problem in the state of art is a weak bond between the capturing molecules and the fiber. Therefore capturing molecules can come off during the collection process or while retracting the fiber. This is a major problem especially for in-vivo application, because the capturing molecules stay in the patient's body and side effects can be caused. For both in-vivo and in-vitro analysis a diagnosis is not possible if to many capturing molecules get lost during the procedure. This is one of the reasons for false positive and false negative results in the state of art. The device of the invention solves this problem in a preferred embodiment, wherein the capturing molecules are connected to the fiber preferred via ionic bond, electrostatic bonds and/or covalent bonds. It is preferred that the capturing molecule layers are deposited and attached to the fiber surface by covalent bonds, ionic bonds, electrostatic bonds and/or other bonds. Liquid phase deposition of the capturing molecules onto the fiber can be utilised as well as deposition from the gas phase. Possible approaches are modification of the polymer surface through plasma treatment, silanisation from the liquid phase, chemical vapour deposition, atomic layer deposition or combinations hereof. Surprisingly capturing molecules bound to the fiber in said way do not come off during the collection of analytes or during retracting the fiber.

Figure 6:
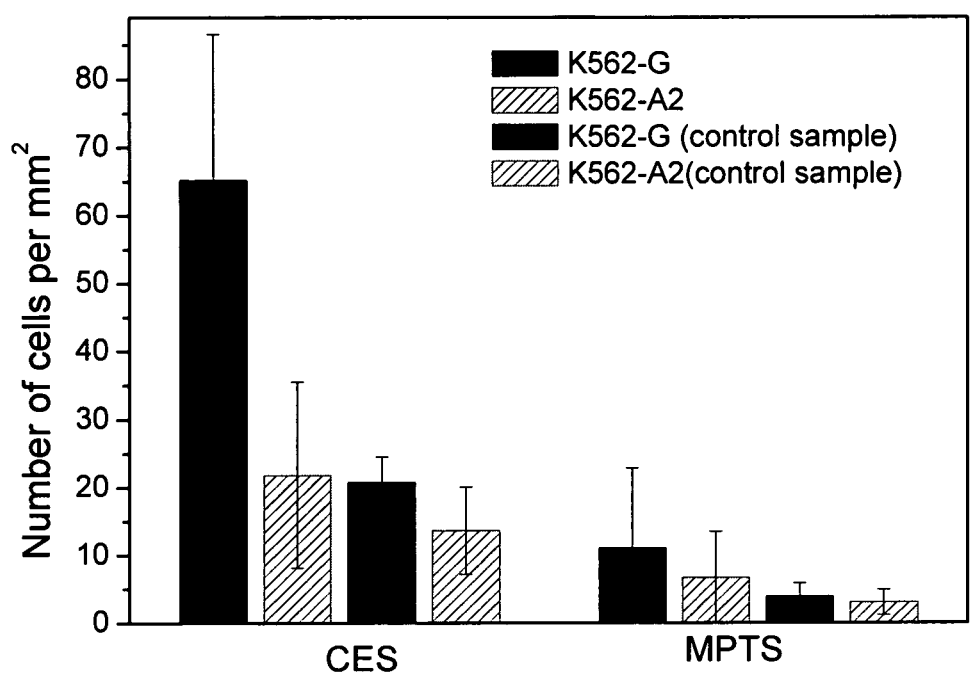

In a preferred embodiment, the polymer fiber is functionalized by silane compounds containing an organo-reactive arm that is used to conjugate different biomolecules to the inorganic substrates. The organosilanes used for these applications include functional or reactive groups such as amino, aldehyde, carboxylate and thiol groups to bind molecules through hydrophobic interactions on polyamide, polystyrene and polypropylene fibers. For the deposition of the functional silanes, aqueous/organic solvent as well as the vapor phase deposition is possible. First results employing polyamide surfaces functionalized with antibodies specific against the HLA-G antigen showed an efficient cell binding. In these experiments the attachment of antibodies was performed on polyamide surfaces covered with Carboxyethylsilanetriol (CES) and 3-Mercaptopropyltrimethoxysilane (MPTS) purchased from Gelest, Inc. The functionalisation was achieved by applying the following steps:

- activation of the polyamide surface using oxygen plasma (Branson International Plasma Corporation) 200 W for 120 seconds.
- vapor phase deposition of CES by using the following parameters: evaporation temperature=65° C., time=30 min.
- vapor phase deposition of MPTS by using the following parameters: evaporation temperature=65° C., time=30 min These surfaces were incubated with F(ab')s and MEMG/9 antibodies in PBS buffer for 1 h at 37° C. After the functionalization with antibodies, the surfaces were incubated with labeled K562-G cells (K562-A2 as a control), so that the detection was possible with fluorescence microscopy. Within the experiments, control samples were also included, that is surfaces functionalized with the different organo silanes but no antibody binding. FIG. 6 shows the statistics obtained from the corresponding images.

Further preferred is a device, wherein the linker molecule binds to the capturing molecule via amine bonds, chelate complexation, ionic bond, electrostatic bonds and/or covalent bonds. Linker molecules and capturing molecules that are able to bind via said bonds are advantageous because the linkers are bound tight enough to secure that they do not come off while the fiber is retracted.

Further preferred is a device additionally comprising passive or passivating molecules, wherein these molecules do not contribute to any binding process. The ratio between these passive or non-capturing molecules and the specifically functional capturing molecules controls the density of capturing sites on the surface of the fiber. The layer of passive molecules or non-capturing molecules is also referred to as "host layer". In order to adjust the density of capturing molecules on the surface these molecules can be effectively diluted by one or more passive molecule species that do not contribute to any binding process.

It is preferred that these passive molecules comprise a material selected from the group comprising polyethyleneglycol, alkane chains and/or other molecules that are bound via silane chemistry or other polymer coupling chemistry to the fiber surface. Polyethyleneglycol has a very low toxicity and can therefore be used in pharmaceutical compositions or devices. A suitable mixture of guest and host molecules is presented to the fiber either in the liquid or in the gas phase.

Preferred is the device, wherein the passive molecules are bound via polymer coupling chemistry, preferred silane chemistry to the fiber. This embodiment leads to a stable introduction of passive molecules to the fiber. It is important that the passive molecules do not come off during the diagnosis method.

One major advantage of the invention is the fact that the density of capturing sites can be adjusted and optimised in order to provide high capture efficiency. Direct immobilisation of for example antibodies without a control of their density and orientation on the surface can limit their binding efficiency. This is important especially for an application, which requires extremely high sensitivities, e.g. detection of analytes at extremely low concentrations. Surprisingly advantageous results could be achieved by using a devise wherein the space between the capturing molecules was 1 nm to 500 nm. The best results could be achieved be using a device wherein the space between the capturing molecules was 10 nm to 100 nm. This embodiment allows straightforward control and optimisation of the density of capturing sites on the fiber surfaces at low costs.

In another preferred embodiment the device further comprises turbulator structures, wherein the turbulator structures are preferably trenches, pits, hollows preferred with Gaussian shape. Also preferred are turbulator structures with a paraboloid shape or a bell shape. In order to enhance the analyte-surface interaction in a fluidic environment, turbulator structures are introduced into the fiber surface by methods like optical lithography, imprint lithography, molding, hot embossing, wet etching, plasma etching or milling. The turbulator structures can be of any shape that locally enhances the effective surface area of the fiber. The turbulator structures which are trenches, pits, hollows with Gaussian shape, paraboloid shape or bell shape are especially preferred because they collect and protect the immobilised analytes during and after the collection process.

Practical experiments in flowing body liquids, e.g. the blood stream inside veins, have shown that the flat surfaces of the fibers known in the state of art do not provide enough turbulence to attract as much analytes as possible towards the fiber surface. By introducing turbulator structures the analyte-surface interaction is optimised which leads in a large analyte-capturing efficiency. The turbulator structures also act as collecting chambers for analytes. When capturing molecules that cover the surface of a turbulator bind to analytes, these analyte are more protected, due to the cavity. This embodiment is especially preferred when the target analytes are whole cells. It is more difficult to bind cells to a device compared to smaller analytes like antibodies. Surprisingly introducing turbulator structures increased the amount of collected cells, due to the fact that less cells get lost because of a weak binding.

Also preferred is the device, wherein the turbulator structures have a width of 100 nm to 2 mm, preferred 50 µm to 1000 µm and a depth of 100 nm to 2 mm, preferred 50 to 100 µm. These sizes result in a superior attraction of analytes.

Therefore it takes less time to collect the analytes, which is less stressful for the patients. Fibers with said turbulator structures are also advantageous for in-vitro application. One of the problems in in-vitro diagnosis is the missing circulation of the sample. Therefore, less analytes get in contact with the device and can be collected. The surface of the fiber is enlarged by turbulator structures, which is why more analytes can be collected, compared to the state of art. Additionally the turbulator structures also cause turbulences in-vitro and thus attract more analytes.

In another preferred embodiment the invention relates to a device, wherein the analyte is selected from the group comprising macromolecules, polynucleotides, RNA, DNA, proteins, marker proteins, lipoproteins, polypeptides, antibodies, autoantibodies, hormones, antigens, cells, CD4 cells, viruses, bacterial cells, parasites, fungus cells, tumour cells, stem cells and/or cells that originate from a foetus during pregnancy, or parts thereof.

Any suitable cells or cell lines can be evaluated, including, but not limited to, differentiated human cells, stem cells, cancer cells, micro-metastases, peripheral blood cells (including peripheral blood mononuclear cells), lymphoid cells, hepatocytes, bone marrow-derived cells, skin biopsies, broncho-alveolar lavage washings, breast tissue cells, kidney cells, oral, urethral, vaginal, cervical, or gastric, or intestinal mucosal cells or mucosal biopsies, reproductive cells, adipose cells, nerve or stromal cells, bone or synovial cells, or other suitable human cell types. Both normal and malignant cells from the tissues mentioned can be captured with the device of the invention.

Especially preferred is the device, for prenatal diagnosis, wherein the analytes are fetal cells in the maternal blood. It is known that some of the fetal cells are in the mothers bloodstream during pregnancy, however the concentration is very low which is why they cannot be detected and collected successfully with methods known in the state of art. Therefore it was very surprising, that it is possible to detect fetal cell in the mother's blood with the device of the invention. Especially turbulator structures and cell protection chambers enable the detection of rare cells like fetal cells. This is a major advantage because diseases and chromosomal abnormalities like the Down syndrome can be detected during pregnancy without the risks of an amniocentesis.

Preferably, the fiber surface is patterned with microstructures

In another preferred embodiment the invention relates to a device, wherein the microstructures are holes with a specific geometry, preferred hemispheres, cylinders, pyramids, frusta or frustums of pyramids. Also preferred is a sphere, an ellipsoid, a paraboloid, a hyperboloid, a polyhedron, a tetrahedron, a cube, a pyramid, an icosahedron, a dodecahedron, an octahedron, a prism, a cone and/or a frustum of a cone. The imprint of efficient microstructures enhances the interaction between analytes and the fiber. Surprisingly not only the interaction is superior but also complications are avoided. Especially non-specific adsorption of other analytes has to be reduced by this embodiment of the invention. A device comprising surface geometries is especially preferred when the device does not comprise any turbulator structures. The employed patterning methods can be optical lithography, imprint lithography, molding, hot embossing, wet etching, plasma etching or milling.

Preferred is a device, wherein the single microstructures (holes) have a width of 15 to 50 µm and a depth of 25-70 µm. In another preferred embodiment, the distance between two holes is 15 to 50 µm. The holes or specific surface geometries or microstructures having these sizes support the concentration of analytes at specific locations on the fiber. Therefore, the capture efficiency is enhanced which allows a more specific and certain diagnosis.

Also preferred is a device, wherein the device can be inserted in-vivo inside an organism, preferred of an animal or human, preferred into solid tissue, more preferred a cavity of the body like the uterus, the amniotic sac, the peritoneum, the gastro intestinal tract, most preferred into an artery or vein, the ureter, an lymphatic vessel and/or the spinal cord. The device of the invention is superior due to its shape, material and flexibility. Therefore the device can be placed into a human or an animal without causing any pain or discomfort.

The device of the invention can be used to obtain samples of tissue, cells or other analytes out of an organism. The organism can be an animal organism or a human organism. The obtained samples of tissues, cells or other analytes can be used for subsequent testing.

Another application is the use of the device of the invention to eliminate tissue, cells or other analytes for example antibodies from the organism.

In another preferred embodiment the invention relates to a use of the device, comprising
(i) introduction of the device into a biological sample,
(ii) binding of the analytes and/or linker molecules to the capturing molecules,
(iii) retraction of the device,
(iv) separation of the analytes and/or linker molecules and/or
(v) analyses of the analytes and/or the linker molecules.

Any material or sample containing or suspected of containing an analyte of interest can be used as biological sample in terms of the invention. For example a biological sample can be a blood sample, a urine sample, a semen sample, a lymphatic fluid sample, a cerebrospinal fluid sample, amniotic fluid sample, a biopsy sample, a needle aspiration biopsy sample, a cancer sample, a tumour sample, a tissue sample, a cell sample, a cell lysate sample, a forensic sample, an infection sample, a nosocomial infection sample, an environmental sample or combinations thereof.

Also preferred is the use of the device, comprising
(i) introduction of the device into an organism,
(ii) binding of the analytes and/or linker molecules to the capturing molecules,
(iii) retraction of the device,
(iv) separation of the analytes and/or linker molecules and/or
(v) analyses of the analytes and/or the linker molecules.

A problem in the state of art is that trapped analytes are often damaged or destroyed while retracting the fiber after capture. The analytes are often destroyed by the mechanical boundaries, so that a detection or diagnosis is not possible anymore. Surprisingly the microstructures of the invention help to protect the captured analytes during retraction. Therefore the error rate is reduced and the device can be used more successfully.

The advantages of the device of the invention compared to other devices arise in a low risk of micro injuries during in-vivo application, the adjustable density of capturing molecules, the optimisation of the capture efficiency, the fact that no metallization is needed, a higher analyte-surface interaction and an efficient protection of the captured analytes during retraction, due to microfluidic surface features which can be introduced by cheap patterning techniques. A great advantage is also the low material and fabrication costs.

The teachings of the present invention are characterised by the following features:
- departure from the beaten track
- a new perception of the problem
- satisfaction of a long-felt need or want
- hitherto all efforts of experts were in vain
- the simplicity of the solution, which proves inventive action, especially since it replaces a more complex doctrine
- the development of scientific technology followed another direction
- the achievement forwards the development
- misconceptions among experts about the solution of the according problem (prejudice)
- technical progress, such as: improvement, increased performance, price-reduction, saving of time, material, work steps, costs or resources that are difficult to obtain, improved reliability, remedy of defects, improved quality, no maintenance, increased efficiency, better yield, augmentation of technical possibilities, provision of another product, opening of a second way, opening of a new field, first solution for a task, spare product, alternatives, possibility of rationalisation, automation or miniaturisation or enrichment of the pharmaceutical fund
- special choice; since a certain possibility, the result of which was unforeseeable, was chosen among a great number of possibilities, it is a patentable lucky choice
- error in citations
- young field of technology
- combined invention; a combination of a number of known elements, with a surprising effect
- licensing
- praise of experts and
- commercial success Said advantages are shown especially in the preferential embodiments of the invention.

FIGURES

FIG. 1 shows the schematic structure of a polymeric fiber 1 with one round-shaped end 2 and one bow-shaped end 3. The surface of the fiber is covered with passivating molecules host-layer 5 and capturing molecules 6, wherein a connecting site 7 binds a linker 4 to the capturing molecule 6. In FIG. 1 the capturing molecule 6 is an antibody, wherein the analyte is an antigen, e.g. on a cell or a secondary antibody. However, the capturing molecule 6 may also be an antigen which is bound to a corresponding antibody representing the analyte.

Figure 2:
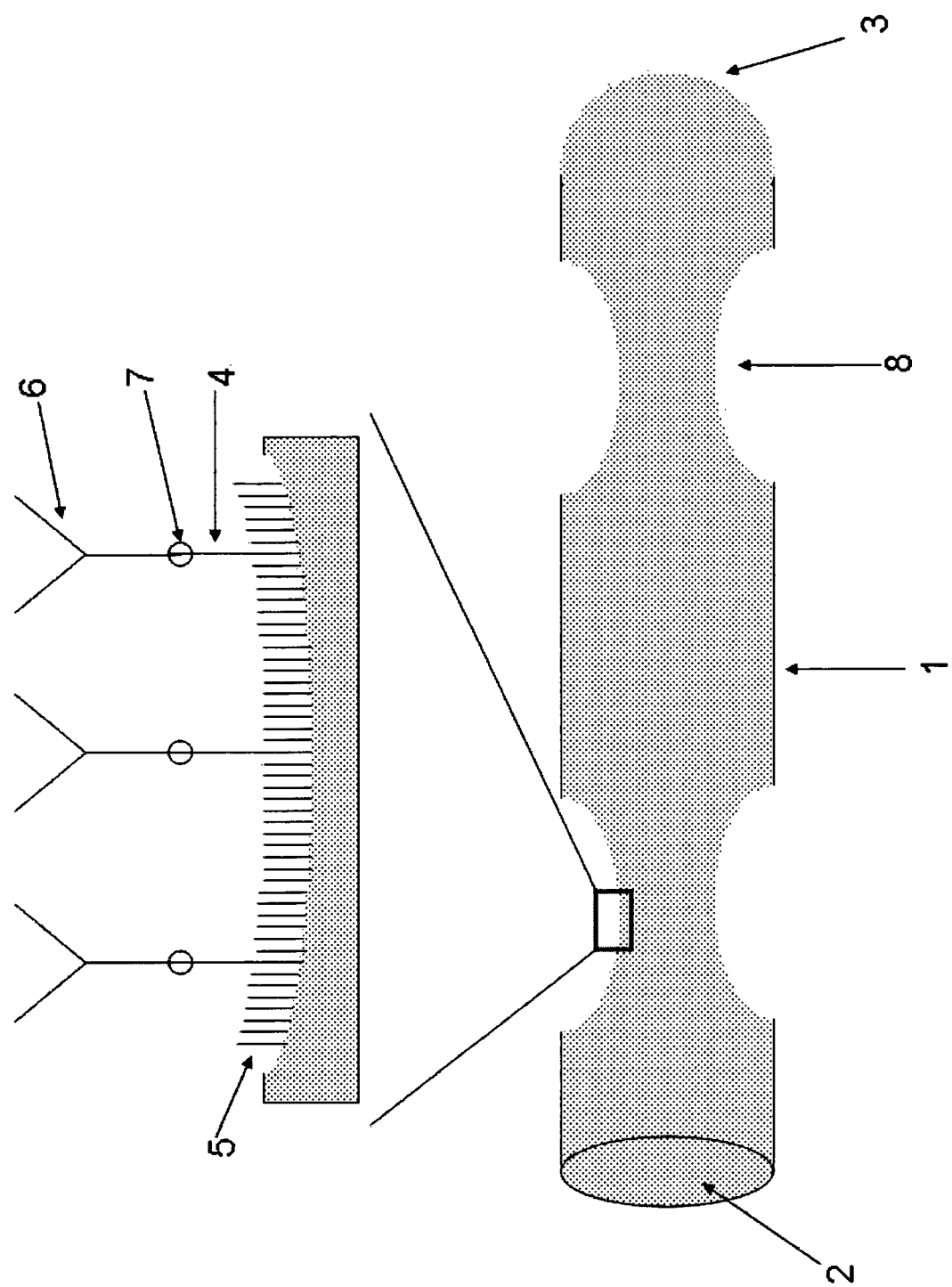

FIG. 2 shows the schematic structure of a polymeric fiber 1, wherein turbulators 8 are imprinted into the surface of the polymer fiber 1. The remaining features of the device are substantially the same as in FIG. 1 and are designated by the same reference numerals.

Figure 3:
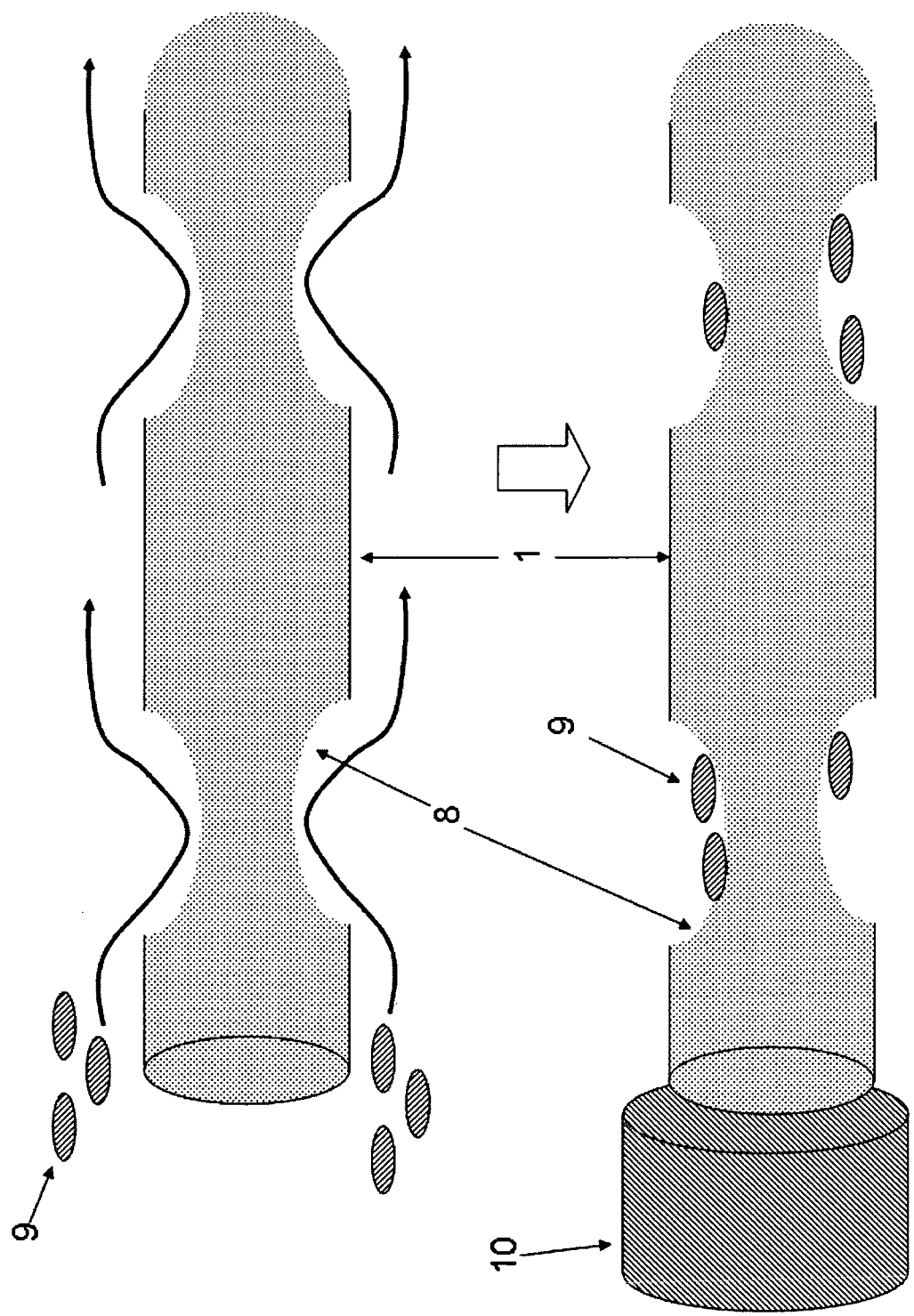

FIG. 3 shows the basic impact of the turbulators 8 on the flow of the sample liquid comprising analytes like cells 9 close to the surface of the fiber 1. The remaining features of the device are substantially the same as in FIG. 2 and are designated by the same reference numerals. A tube 10 will be used to cover the fiber 1 after the detection step. After binding the analyte, the tube 10 including the fiber 1 will be retracted from the blood vessel or vein. Subsequently, the tube 10 will be removed and the analytes will be detached. Thereafter, the detached analytes will be identified and characterized using suitable and appropriate methods. In the case of cells, DNA will be gathered from the core of the cells and will be amplified by PCR, for example.

Figure 4:
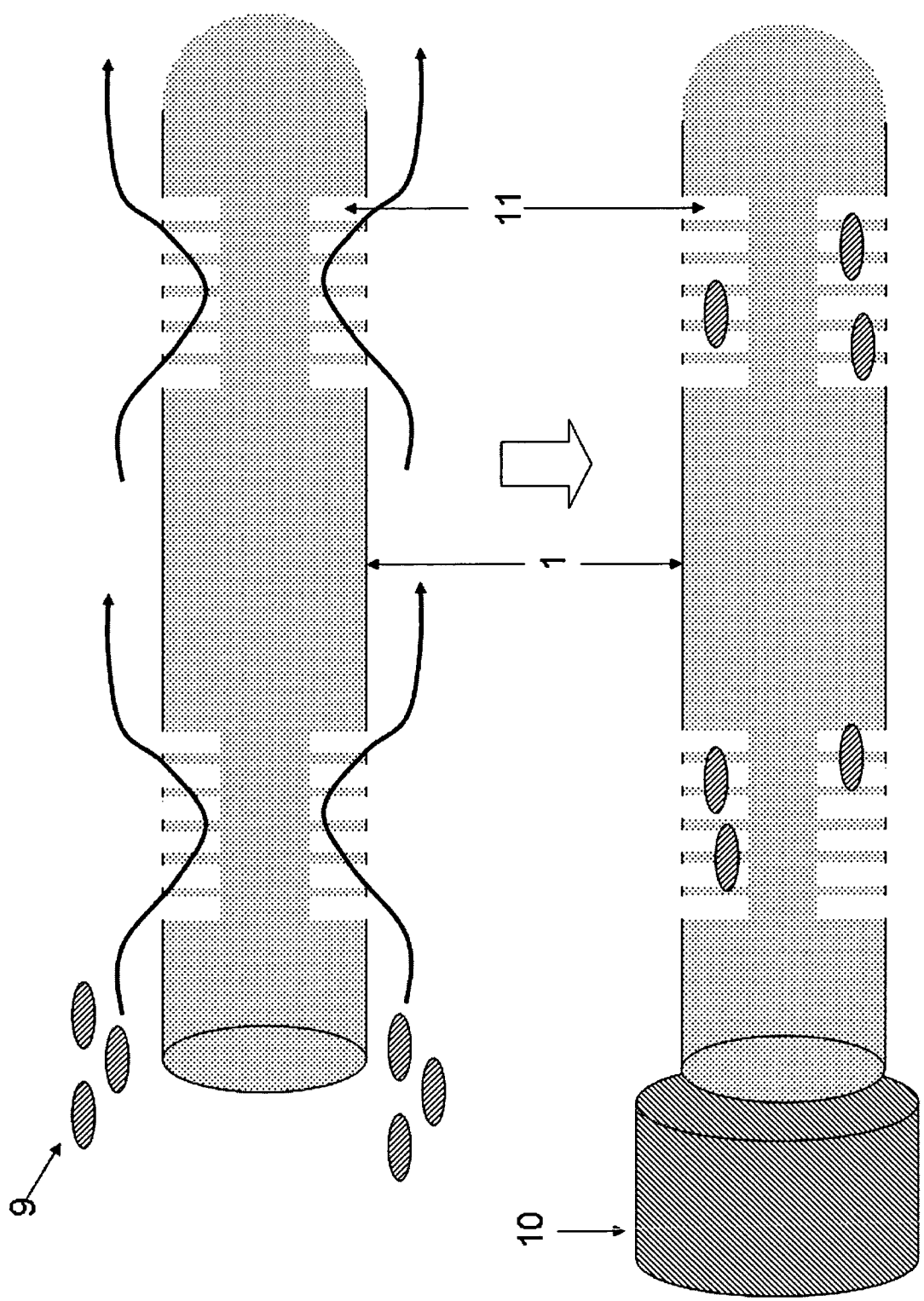

FIG. 4 shows a variation of the turbulator structure as compared to the devices according to FIG. 2 or 3. In this case, tree-like structures 11 are imprinted into the fiber surface 1. The remaining features of the device are substantially the same as in FIG. 2 or 3 and are designated by the same reference numerals.

Figure 5:
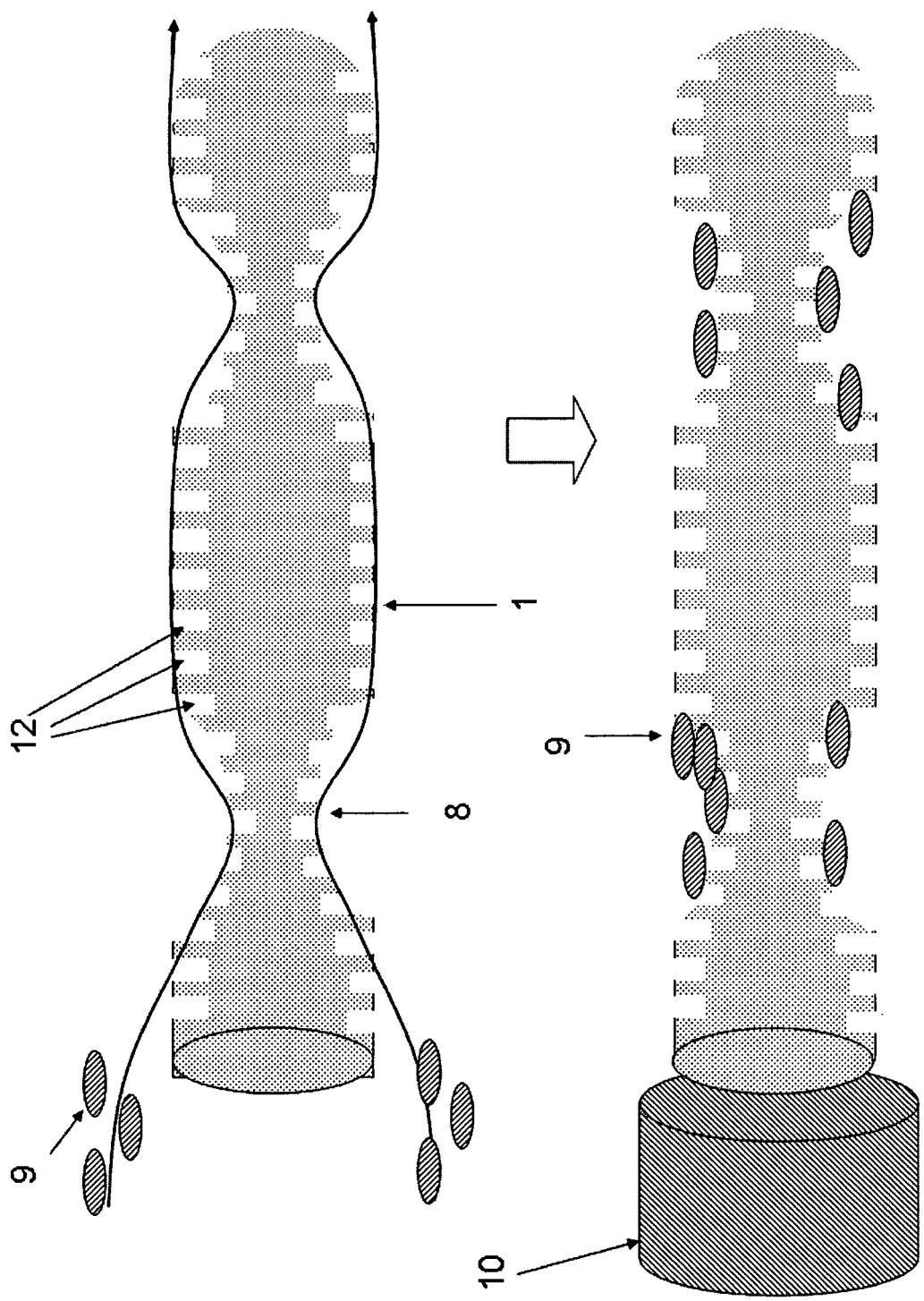

FIG. 5 shows the turbulator structures 8 and the patterning of the whole surface of the fiber with microstructures 12. In this case, the microstructures 12 are holes with specific geometry of a cylinder. The sizes of the turbulator structures 8 are about 50 to 1000 μm in width, i.e. parallel to the fiber axis and/or in the circumferential direction of the fiber, and about 50 to 100 μm in height, i.e. radial to the fiber axis. The sizes of the microstructures 12 are about 15 to 50 μm in width, i.e. parallel to the fiber axis, and about 25 to 70 μm in height, i.e. radial to the fiber axis. The distances of the microstructures 12 are about 15 to 50 μm in the axial and/or the circumferential direction of the fiber.

FIG. 6 shows the number of cells bound onto the polyamide surfaces functionalized using different organo silane compounds. The statistics was obtained from the fluorescence microscopy images.

The invention claimed is:

1. A device for detecting analytes, comprising a polymer fiber and capturing molecules,
   wherein each capturing molecule binds to an analyte and/or a linker molecule,
   wherein the device comprises turbulator structures, wherein the turbulator structures are trenches, pits or hollows,
   wherein the capturing molecules are present on a surface of the turbulator structures, and
   wherein the turbulator structures are formed on a surface of the polymer fiber.

2. The device according to claim 1, wherein the polymer fiber is flexible.

3. The device according to claim 1, wherein the polymer fiber has a shape of a cylinder or a tube.

4. The device according to claim 1, wherein the fiber is round-shaped or bow-shaped at one or both ends of the fiber.

5. The device according to claim 1, wherein a diameter of the fiber is 100 μm to 3 mm.

6. The device according to claim 1, wherein the fiber comprises a material selected from the group consisting of nylon, polyimide, Teflon, polyurethane, polystyrene, polyethylene, epoxy, polycarbonate and composite materials thereof.

7. The device according to claim 1, wherein the capturing molecules are selected from the group consisting of antibodies, antigens, receptors, polynucleotides, polypeptides, DNA probes, RNA probes, proteins and cells.

8. The device according to claim 1, wherein the capturing molecules bind to linker molecules.

9. The device according to claim 1, wherein the capturing molecules are connected to the polymeric fiber.

10. The device according to claim 1 comprising passive molecules on a surface of the polymer fiber, wherein the passive molecules do not contribute to any binding process to the analyte.

11. The device according to claim 10, wherein the passive molecules are bound via polymer coupling chemistry and/or silane chemistry to a surface of the polymer fiber.

12. The device according to claim 10, wherein the passive molecules comprise a material selected from the group consisting of polyethyleneglycol and alkane chains.

13. The device according to claim 1, wherein the space between the capturing molecules is 1 nm to 500 nm.

14. The device according to claim 1, wherein the turbulator structures have a width of 100 nm to 2 mm.

15. The device according to claim 1, wherein the analyte is selected from the group consisting of macromolecules, polynucleotides, RNA, DNA, proteins, lipoproteins, polypeptides, antibodies, autoantibodies, hormones, antigens, cells, tumour cells, marker proteins and/or cells that originate from a foetus during pregnancy and erythroidal cells.

16. The device according to claim 1 for prenatal diagnosis, wherein the analytes bound by the capturing molecules are cells that originate from a foetus during pregnancy and wherein said cells are collected from maternal blood.

17. The device according to claim 11, wherein the fiber surface is patterned with microstructures.

18. The device according to claim 17, wherein the microstructures are holes.

19. The device according to claim 18, wherein the holes have a width of 15 to 50 µm and a depth of 25 to 70 µm.

20. The device according to claim 18, wherein a distance between two holes is 15 to 50 µm.

21. The device according to claim 1, in combination with, and inserted in-vivo inside an organism.

22. The device according to claim 1, wherein the turbulator structures are trenches, pits or hollows with a Gaussian shape, parabolic shape or bell-shape.

23. The device according to claim 1, wherein the turbulator structures have a width of 100 nm to 2 mm and a depth of 100 nm to 2 mm.

24. The device according to claim 1, wherein the turbulator structures are integrally formed with the polymer fiber.

25. The device according to claim 1, wherein the turbulator structures are introduced into the surface of the polymer fiber by optical lithography, imprint lithography, molding, hot embossing, wet etching, plasma etching, or milling.

26. The device according to claim 1, wherein each capturing molecule is bound to the surface of the turbulator structures at a connecting site via the linker molecule, wherein the linker molecule is bound to the polymer fiber.

27. The device according to claim 1, wherein each capturing molecule is chemically bound to the surface of the turbulator structures of the polymer fiber.

28. A method for detecting analytes via a device for detecting analytes comprising a polymeric fiber and capturing molecules, wherein the capturing molecules bind to analytes and/or linker molecules, wherein the device comprises turbulator structures, wherein the turbulator structures are trenches, pits or hollows, wherein the capturing molecules are present on a surface of the turbulator structures, and wherein the turbulator structures are formed on a surface of the polymer fiber, the method comprising:
    (i) introduction of the device into a biological sample,
    (ii) binding of the analytes and/or linker molecules to the capturing molecules,
    (iii) retraction of the device,
    (iv) separation of the analytes and/or linker molecules and/or capturing molecules,
    (v) analysis of the analytes.

29. The method according to claim 28, comprising:
    (i) introduction of the device into an organism as the biological sample.

30. The method according to claim 28, wherein each capturing molecule is chemically bound to the surface of the turbulator structures at a connecting site via the linker molecule, wherein the linker molecule is bound to the polymer fiber.

31. The method according to claim 28, wherein in step (i), the device is inserted in-vivo inside an organism.

32. The method according to claim 30, wherein the biological sample includes a vein of a living organism.

33. The method according to claim 30, wherein the biological sample includes a blood sample, a urine sample, a semen sample, a lymphatic fluid sample, a cerebrospinal fluid sample, an amniotic fluid sample, a biopsy sample, a needle aspiration biopsy sample, a cancer sample, a tumor sample, a tissue sample, a cell sample, a cell lysate sample, a forensic sample, an infection sample, or a nosocomial infection sample.

34. The method according to claim 28, wherein each capturing molecule is chemically bound to the surface of the turbulator structures of the polymer fiber.

* * * * *